United States Patent [19]

Rudberg

[11] 4,196,427
[45] Apr. 1, 1980

[54] METHOD AND APPARATUS FOR MEASURING LOW CONCENTRATIONS OF CHLORINE AND CHLORINE OXIDE

[76] Inventor: Harry I. A. Rudberg, Box 6040, S-102 31 Stockholm, Sweden

[21] Appl. No.: 867,706

[22] Filed: Jan. 9, 1978

Related U.S. Application Data

[63] Continuation-in-part of Ser. No. 709,424, Jul. 28, 1976, abandoned.

[51] Int. Cl.² ............................................. C08B 17/10
[52] U.S. Cl. .................................. 340/634; 23/232 E; 338/34
[58] Field of Search ................... 340/634, 632; 338/34; 73/23; 23/232 E

[56] References Cited

U.S. PATENT DOCUMENTS 3,609,732  9/1971  Kasahara ............................. 340/634

Primary Examiner—John W. Caldwell, Sr.
Assistant Examiner—Daniel Myer
Attorney, Agent, or Firm—Brady, O'Boyle & Gates

[57] ABSTRACT

A semiconductor sensor element having two filaments of a noble metal, preferably platinum, embedded in spaced apart relation in a body of titanium oxide. One of the filaments serves as a sensing filament. The other filament is supplied with current at a high voltage, suitably about 100 volts. The resistance of the sensing filament increases sharply in the presence of gaseous chlorine or chlorine compounds, and this change in resistance is used to actuate an alarm or the like.

10 Claims, 3 Drawing Figures

METHOD AND APPARATUS FOR MEASURING LOW CONCENTRATIONS OF CHLORINE AND CHLORINE OXIDE

CROSS-REFERENCE TO RELATED APPLICATION

This application is a continuation-in-part of my earlier application Ser. No. 709,424, filed July 28, 1976, now abandoned.

BACKGROUND TO THE INVENTION

This invention relates to the detection of gaseous chlorine and chlorine compounds by means of semiconductor sensors.

Semiconductor devices are known for detecting the presence of small amounts of various gases in air. Typically, a sensing electrode is embedded in a substrate of semiconducting metal oxide, the conductivity of the sensing electrode varying with exposure of the substrate to certain gases. It is also known to provide a resistive heater within the substrate. One example of such a sensor is disclosed in U.S. Pat. No. 3,676,820.

However, the known semiconductor gas sensors are not capable of detecting the presence of chlorine or chlorine compounds in the atmosphere. Indeed, many known sensors are formed of materials which are decomposed by chlorine.

U.S. Pat. No. 3,695,848 discloses a number of forms of semiconductor gas sensor using a variety of semiconductor materials, such as ZnO, $SnO_2$, $Fe_2O_3$, $TiO_2$, $V_2O_5$, $MnO_2$, $WO_3$, $ThO_2$, $MoO_3$, CdO, and $PbCrO_4$. However, this prior specification does not teach any method for the detection of chlorine and its compounds, and it would not be possible from the disclosure of this prior specification to practice such detection.

SUMMARY OF THE INVENTION

An object of the present invention is to provide a method and an apparatus for the detection of chlorine and chlorine compounds.

To this end, one aspect of the invention provides a method of detecting chlorine and its compounds by the use of a semiconductor sensor element. The sensor element comprises a body of titanium oxide in which are embedded a pair of spaced noble metal filaments, preferably of platinum. Across one of the filaments is applied a voltage of at least 100 volts. The resistance of the other filament is monitored, and increases in the presence of chlorine and its compounds to provide a warning signal.

From another aspect, the invention provides an apparatus for the detection of chlorine and its compounds. The apparatus includes a sensor element of the type defined in the preceding paragraph. A power supply circuit is connected to supply a voltage of at least 100 volts to one of the filaments of the sensor element. A gate means is controlled by the resistance of the other filament to provide a warning output when said resistance reaches a predetermined level corresponding to a given chlorine concentration. The said other filament suitably forms part of a potential divider. The gate means may be an SCR or a flip-flop circuit. The gate means may be connected to enerize a relay.

BRIEF DESCRIPTION OF THE DRAWINGS

Other objects and advantages of the invention will be apparent from the following description of a preferred embodiment thereof given by way of example with reference to the accompanying drawings, in which.

DESCRIPTION OF THE PREFERRED EMBODIMENT

Figure 1:
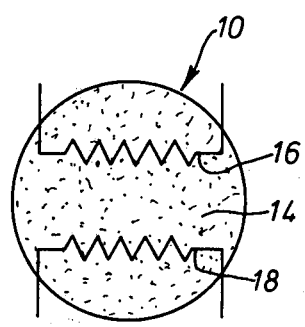
FIG. 1 is a schematic cross-sectional view of a sensor element for use in the present invention.
Figure 2:
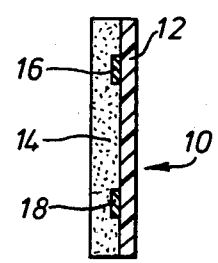
FIG. 2 is a side view of the element of FIG. 1, partly in cross-section.

Referring to FIGS. 1 and 2, a sensor element 10 comprises a dielectric substrate 12 having formed thereon a layer 14 of titanium oxide semiconductor. Platinum filaments 16 and 18 are embedded in the titanium oxide layer 14 in spaced-apart relationship. To manufacture such a sensor element, the filaments 16, 18 are suitably deposited on the substrate by high vacuum vaporization while simultaneously the titanium oxide layer 14 is sintered by radio frequency induction heating.

Figure 3:
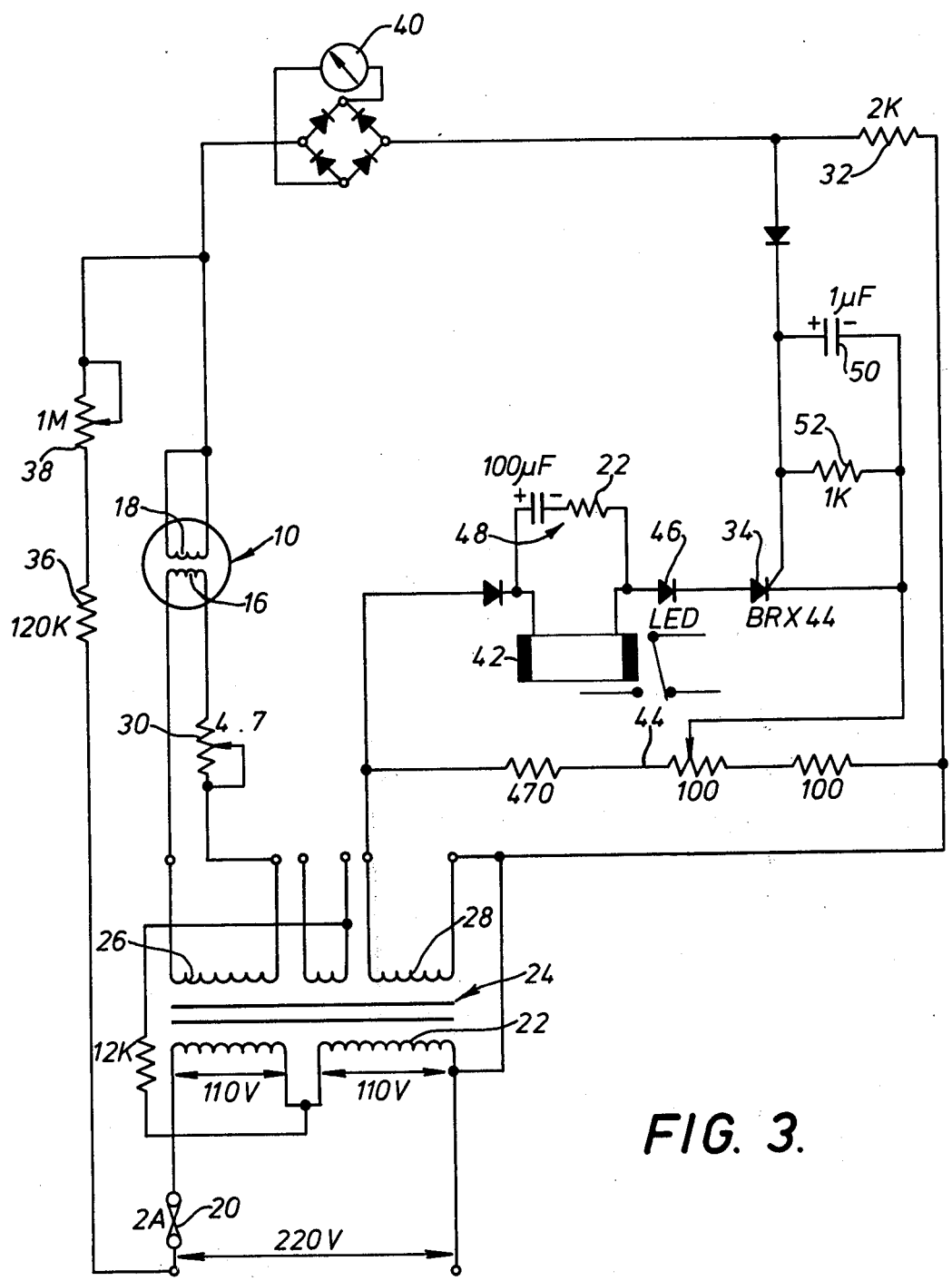
FIG. 3 is a circuit diagram of a chlorine detecting apparatus embodying the invention.

Referring to FIG. 3, a 220 volt A.C. supply is applied via a fuse 20 to the center-tapped primary 22 of a transformer 24. The transformer 24 has two independent secondaries 26, 28 each providing an A.C. output of about 110 volts. One secondary 26 is connected to supply the filament 16 of the sensor element 10. A low value potentiometer 30 is connected in this circuit to allow adjustment of the voltage applied to the filament in the region of 100 volts.

The other filament 18 of the element 10 is connected as a variable resistance in a sensing circuit. The filament 18 forms a potential divider with a resistance 32, the voltage at the junction of these being used to control an SCR 34. Resistor 36 and potentiometer 38 are connected in parallel with the sensor 10; the potentiometer may be adjusted to control the sensitivity of the sensor. A voltmeter 40 supplied by a diode bridge interposed between the filament 18 and the resistor 32 provides a reading of chlorine concentration.

The SCR 34 is connected in series with a relay coil 42 across the transformer secondary 28 via a variable resistance chain 44. The series circuit also includes a light emitting diode 46. An RC circuit 48 is provided across the relay coil 42 to suppress switching surges. A capacitor 50 and resistor 52 are provided in parallel across the gate circuit of the SCR 34 to ensure turn-off.

Thus, when the concentration of chlorine or chlorine compounds at the sensor element 10 reaches a predetermined level set by the resistances 38 and 44, the SCR 34 is turned on and the relay coil 42 is energized. The relay contacts may be used to activate an audible and/or visible alarm, or to turn off an electrical equipment controlled by the apparatus. At the same time, the LED 46 is turned on to give a visible indication.

I am aware that sensor elements similar to the element 10 described above are known in the art, for example from U.S. Pat. No. 3,695,848 referred to above. However, these have not hitherto been used in the art in a manner which allows the detection of chlorine and its compounds. The prior art has taught the energization of semiconductor gas sensors at low voltages, typically in the region of 15 volts. Used in this way, chlorine is not detected. I have discovered that by energization a sensor of the above type at a high voltage of about 90 to 120 volts, preferably about 100 volts, chlorine can be reliably and easily detected. It is believed that when the sensor is energized in this way and chlorine atoms are present at the surface of the semiconductor, electrons are drawn from the semiconductor to combine with the gas, thus reducing the conductivity of the sensor.

It will be appreciated that modifications of the above described embodiment may be made within the spirit and scope of the invention. For example, instead of using a relatively thin layer of titanium oxide on a substrate with evaporated filaments, the filaments may be formed from wire and embedded in a body, such as a sphere, of sintered titanium oxide. The sensor may also be energized by D.C. current of about 100 volts. It will be understood that references to A.C. voltages are to the root-mean-square value of such voltages.

I claim:

1. A method of detecting the presence of low concentrations of chlorine and compounds thereof in air, comprising exposing a sensor element in the form of a pair of spaced noble metal filaments embedded in a body of titanium oxide to gaseous chlorine or compounds thereof in air, energizing one of said filaments with a voltage of at least 90 volts, monitoring the resistance of the other said filament, and detecting the presence of gaseous chlorine or compounds thereof upon an increase in the resistance of the other said filament during the monitoring step.

2. The method of claim 1, wherein said voltage is about 100 volts.

3. Apparatus for detecting the presence of low concentrations of gaseous chlorine and compounds thereof, comprising a sensor element including a pair of spaced noble metal filaments embedded in a body of titanium oxide, a source of A.C. power, power transformer means having a primary winding with opposite ends connected across said source of A.C. power, said power transformer means having secondary winding means, one of said filaments connected to said secondary winding means, said secondary winding means adapted to apply a potential of at least 90 volts across said one filament, a resistance connected between the other of said filaments and one side of said source of A.C. power and forming a potential divider circuit, said other filament adapted to increase in resistance when said sensor element is exposed to gaseous chlorine or compounds thereof, a junction between said other filament and said resistance, a resistance circuit connected between the other side of said source of A.C. power and said junction, and detector means connected between said junction and secondary winding means and responsive to provide an output signal indicating the presence of gaseous chlorine or compounds thereof when the resistance of said other filament rises above a predetermined level.

4. The apparatus of claim 3, wherein said filaments are of platinum.

5. The apparatus of claim 3, wherein said body of titanium oxide and said filaments are deposited on a substrate.

6. The apparatus of claim 3, wherein said secondary winding means is adapted to apply a voltage of about 100 volts to said one filament.

7. The apparatus of claim 3, wherein said detector means comprises a controlled switching device having a control electrode connected to said junction of said resistance and said other filament.

8. The apparatus of claim 7, wherein said controlled switching device is an SCR.

9. The apparatus of claim 7, wherein said controlled switching device is connected to control the energization of a relay.

10. The apparatus of claim 7, including a light emitting diode in series with said controlled switching device.

* * * * *